(12) United States Patent
Vale et al.

(10) Patent No.: US 11,642,145 B2
(45) Date of Patent: May 9, 2023

(54) GUIDEWIRE WITH AN ATRAUMATIC CLOT-CIRCUMVENTING CONFIGURED DISTAL END FOR USE IN AN ENDOVASCULAR MEDICAL SYSTEM

(71) Applicant: Neuravi Limited, Galway (IE)

(72) Inventors: David Vale, Barna (IE); Michael Gilvarry, Headford (IE)

(73) Assignee: NEURAVI LIMITED, Galway (IE)

( * ) Notice: Subject to any disclaimer, the term of this patent is extended or adjusted under 35 U.S.C. 154(b) by 463 days.

(21) Appl. No.: 16/857,372

(22) Filed: Apr. 24, 2020

(65) Prior Publication Data

US 2020/0246031 A1 Aug. 6, 2020

Related U.S. Application Data

(62) Division of application No. 16/003,527, filed on Jun. 8, 2018, now Pat. No. 10,667,833.

(51) Int. Cl.
*A61B 17/221* (2006.01)
*A61B 17/22* (2006.01)

(52) U.S. Cl.
CPC .... *A61B 17/221* (2013.01); *A61B 2017/2212* (2013.01); *A61B 2017/22044* (2013.01); *A61B 2017/22094* (2013.01)

(58) Field of Classification Search
CPC .......... A61B 17/221; A61B 17/320758; A61B 17/320725; A61B 17/320783; A61B 2017/22044
See application file for complete search history.

(56) References Cited

U.S. PATENT DOCUMENTS

| | | | |
|---|---|---|---|
| 5,425,765 A | 6/1995 | Tiefenbrun et al. | |
| 6,277,139 B1 * | 8/2001 | Levinson | A61B 17/221 606/127 |
| 6,866,677 B2 | 3/2005 | Douk et al. | |
| 9,532,792 B2 | 1/2017 | Galdonik et al. | |
| 9,532,873 B2 | 1/2017 | Kelley | |
| 9,533,344 B2 | 1/2017 | Monetti et al. | |
| 9,539,011 B2 | 1/2017 | Chen et al. | |
| 9,539,022 B2 | 1/2017 | Bowman | |
| 9,539,122 B2 | 1/2017 | Burke et al. | |
| 9,539,382 B2 | 1/2017 | Nelson | |
| 9,549,830 B2 | 1/2017 | Bruszewski et al. | |
| 9,554,805 B2 | 1/2017 | Tompkins et al. | |
| 9,561,125 B2 | 2/2017 | Bowman et al. | |
| 9,572,982 B2 | 2/2017 | Burnes et al. | |
| 9,579,484 B2 | 2/2017 | Barnell | |
| 9,585,642 B2 | 3/2017 | Dinsmoor et al. | |

(Continued)

*Primary Examiner* — Vi X Nguyen
(74) *Attorney, Agent, or Firm* — Cohen & Hildebrand, PLLC

(57) ABSTRACT

An endovascular medical system for use with a clot located in a target vessel. The system including a guidewire formed by a core wire. The guidewire extending in a longitudinal direction from a proximal end to an opposite atraumatic clot-circumventing configured distal end; and a lateral direction of the atraumatic clot-circumventing configured distal end of the guidewire being defined transverse to the longitudinal direction of the guidewire. The atraumatic clot-circumventing configured distal end is designed to prevent injury to an inner wall of the target vessel and prohibit insertion of any portion of the guidewire into a perforator vessel.

16 Claims, 8 Drawing Sheets

(56) References Cited

U.S. PATENT DOCUMENTS

| | | | |
|---|---|---|---|
| 9,615,832 B2 | 4/2017 | Bose et al. | |
| 9,615,951 B2 | 4/2017 | Bennett et al. | |
| 9,622,753 B2 | 4/2017 | Cox | |
| 9,636,115 B2 | 5/2017 | Henry et al. | |
| 9,636,439 B2 | 5/2017 | Chu et al. | |
| 9,642,675 B2 | 5/2017 | Werneth et al. | |
| 9,655,633 B2 | 5/2017 | Leynov et al. | |
| 9,655,645 B2 | 5/2017 | Staunton | |
| 9,655,989 B2 | 5/2017 | Cruise et al. | |
| 9,662,129 B2 | 5/2017 | Galdonik et al. | |
| 9,662,238 B2 | 5/2017 | Dwork et al. | |
| 9,662,425 B2 | 5/2017 | Lilja et al. | |
| 9,668,898 B2 | 6/2017 | Wong | |
| 9,675,477 B2 | 6/2017 | Thompson | |
| 9,675,782 B2 | 6/2017 | Connolly | |
| 9,676,022 B2 | 6/2017 | Ensign et al. | |
| 9,692,557 B2 | 6/2017 | Murphy | |
| 9,693,852 B2 | 7/2017 | Lam et al. | |
| 9,700,262 B2 | 7/2017 | Janik et al. | |
| 9,700,399 B2 | 7/2017 | Acosta-Acevedo | |
| 9,717,421 B2 | 8/2017 | Griswold et al. | |
| 9,717,500 B2 | 8/2017 | Tieu et al. | |
| 9,717,502 B2 | 8/2017 | Teoh et al. | |
| 9,724,103 B2 | 8/2017 | Cruise et al. | |
| 9,724,526 B2 | 8/2017 | Strother et al. | |
| 9,750,565 B2 | 9/2017 | Bloom et al. | |
| 9,757,260 B2 | 9/2017 | Greenan | |
| 9,764,111 B2 | 9/2017 | Gulachenski | |
| 9,770,251 B2 | 9/2017 | Bowman et al. | |
| 9,770,577 B2 | 9/2017 | Li et al. | |
| 9,775,621 B2 | 10/2017 | Tompkins et al. | |
| 9,775,706 B2 | 10/2017 | Peterson et al. | |
| 9,775,732 B2 | 10/2017 | Khenansho | |
| 9,788,800 B2 | 10/2017 | Mayoras, Jr. | |
| 9,795,391 B2 | 10/2017 | Saatchi et al. | |
| 9,801,980 B2 | 10/2017 | Karino et al. | |
| 9,808,599 B2 | 11/2017 | Bowman et al. | |
| 9,833,252 B2 | 12/2017 | Sepetka et al. | |
| 9,833,604 B2 | 12/2017 | Lam et al. | |
| 9,833,625 B2 | 12/2017 | Waldhauser et al. | |
| 2016/0143653 A1* | 5/2016 | Vale | A61F 2/013 606/114 |
| 2017/0007264 A1 | 1/2017 | Cruise et al. | |
| 2017/0007265 A1 | 1/2017 | Guo et al. | |
| 2017/0020670 A1 | 1/2017 | Murray et al. | |
| 2017/0020700 A1 | 1/2017 | Bienvenu et al. | |
| 2017/0027640 A1 | 2/2017 | Kunis et al. | |
| 2017/0027692 A1 | 2/2017 | Bonhoeffer et al. | |
| 2017/0027725 A1 | 2/2017 | Argentine | |
| 2017/0035436 A1 | 2/2017 | Morita | |
| 2017/0035567 A1 | 2/2017 | Duffy | |
| 2017/0042548 A1 | 2/2017 | Lam | |
| 2017/0049596 A1 | 2/2017 | Schabert | |
| 2017/0071737 A1 | 3/2017 | Kelley | |
| 2017/0072452 A1 | 3/2017 | Monetti et al. | |
| 2017/0079671 A1 | 3/2017 | Morero et al. | |
| 2017/0079680 A1 | 3/2017 | Bowman | |
| 2017/0079766 A1 | 3/2017 | Wang et al. | |
| 2017/0079767 A1 | 3/2017 | Leon-Yip | |
| 2017/0079812 A1 | 3/2017 | Lam et al. | |
| 2017/0079817 A1 | 3/2017 | Sepetka et al. | |
| 2017/0079819 A1 | 3/2017 | Pung et al. | |
| 2017/0079820 A1 | 3/2017 | Lam et al. | |
| 2017/0086851 A1 | 3/2017 | Wallace et al. | |
| 2017/0086996 A1 | 3/2017 | Peterson et al. | |
| 2017/0095259 A1 | 4/2017 | Tompkins et al. | |
| 2017/0100126 A1 | 4/2017 | Bowman et al. | |
| 2017/0100141 A1 | 4/2017 | Morero et al. | |
| 2017/0100143 A1 | 4/2017 | Grandfield | |
| 2017/0100183 A1 | 4/2017 | Iaizzo et al. | |
| 2017/0113023 A1 | 4/2017 | Steingisser et al. | |
| 2017/0147765 A1 | 5/2017 | Mehta | |
| 2017/0151032 A1 | 6/2017 | Loisel | |
| 2017/0165062 A1 | 6/2017 | Rothstein | |
| 2017/0165065 A1 | 6/2017 | Rothstein et al. | |
| 2017/0165454 A1 | 6/2017 | Tuohy et al. | |
| 2017/0172581 A1 | 6/2017 | Bose et al. | |
| 2017/0172766 A1 | 6/2017 | Vong et al. | |
| 2017/0172772 A1 | 6/2017 | Khenansho | |
| 2017/0189033 A1 | 7/2017 | Sepetka et al. | |
| 2017/0189035 A1 | 7/2017 | Porter | |
| 2017/0215902 A1 | 8/2017 | Leynov et al. | |
| 2017/0216484 A1 | 8/2017 | Cruise et al. | |
| 2017/0224350 A1 | 8/2017 | Shimizu et al. | |
| 2017/0224355 A1 | 8/2017 | Bowman et al. | |
| 2017/0224467 A1 | 8/2017 | Piccagli et al. | |
| 2017/0224511 A1 | 8/2017 | Dwork et al. | |
| 2017/0224953 A1 | 8/2017 | Tran et al. | |
| 2017/0231749 A1 | 8/2017 | Perkins et al. | |
| 2017/0252064 A1 | 9/2017 | Staunton | |
| 2017/0265983 A1 | 9/2017 | Lam et al. | |
| 2017/0281192 A1 | 10/2017 | Tieu et al. | |
| 2017/0281331 A1 | 10/2017 | Perkins et al. | |
| 2017/0281344 A1 | 10/2017 | Costello | |
| 2017/0281909 A1 | 10/2017 | Northrop et al. | |
| 2017/0281912 A1 | 10/2017 | Melder et al. | |
| 2017/0290593 A1 | 10/2017 | Cruise et al. | |
| 2017/0290654 A1 | 10/2017 | Sethna | |
| 2017/0296324 A1 | 10/2017 | Argentine | |
| 2017/0296325 A1 | 10/2017 | Marrocco et al. | |
| 2017/0303939 A1 | 10/2017 | Greenhalgh et al. | |
| 2017/0303942 A1 | 10/2017 | Greenhalgh et al. | |
| 2017/0303947 A1 | 10/2017 | Greenhalgh et al. | |
| 2017/0303948 A1 | 10/2017 | Wallace et al. | |
| 2017/0304041 A1 | 10/2017 | Argentine | |
| 2017/0304097 A1 | 10/2017 | Corwin et al. | |
| 2017/0304595 A1 | 10/2017 | Nagasrinivasa et al. | |
| 2017/0312109 A1 | 11/2017 | Le | |
| 2017/0312484 A1 | 11/2017 | Shipley et al. | |
| 2017/0316561 A1 | 11/2017 | Helm et al. | |
| 2017/0319826 A1 | 11/2017 | Bowman et al. | |
| 2017/0333228 A1 | 11/2017 | Orth et al. | |
| 2017/0333236 A1 | 11/2017 | Greenan | |
| 2017/0333678 A1 | 11/2017 | Bowman et al. | |
| 2017/0340383 A1 | 11/2017 | Bloom et al. | |
| 2017/0348014 A1 | 12/2017 | Wallace et al. | |
| 2017/0348514 A1 | 12/2017 | Guyon et al. | |

\* cited by examiner

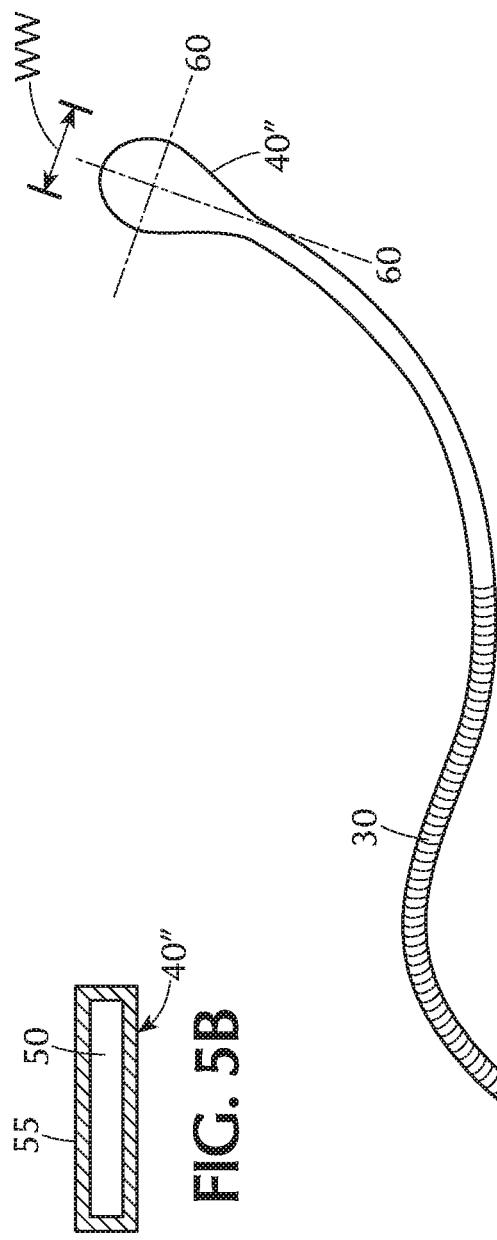
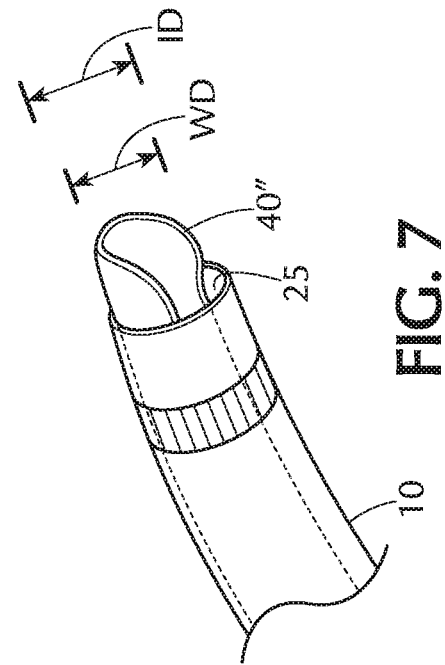
FIG. 5A
FIG. 5B
FIG. 6
FIG. 7

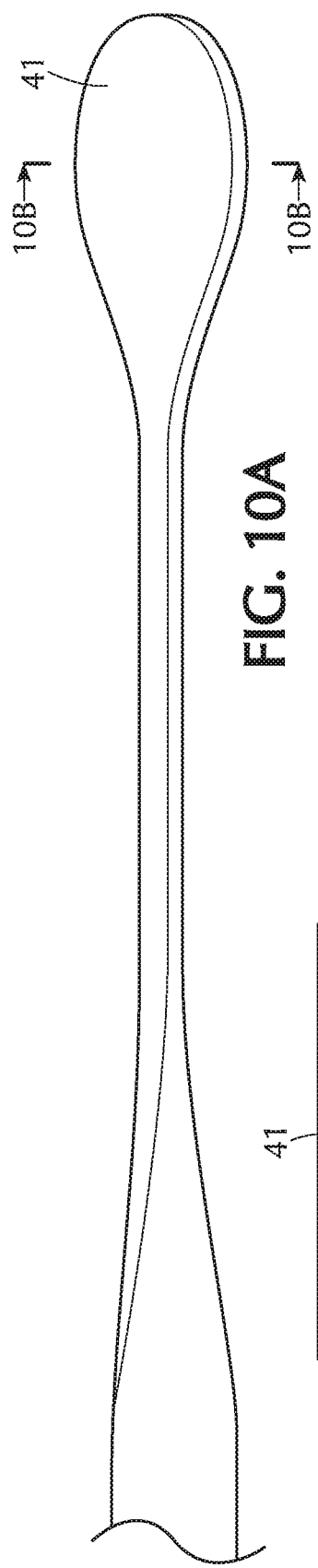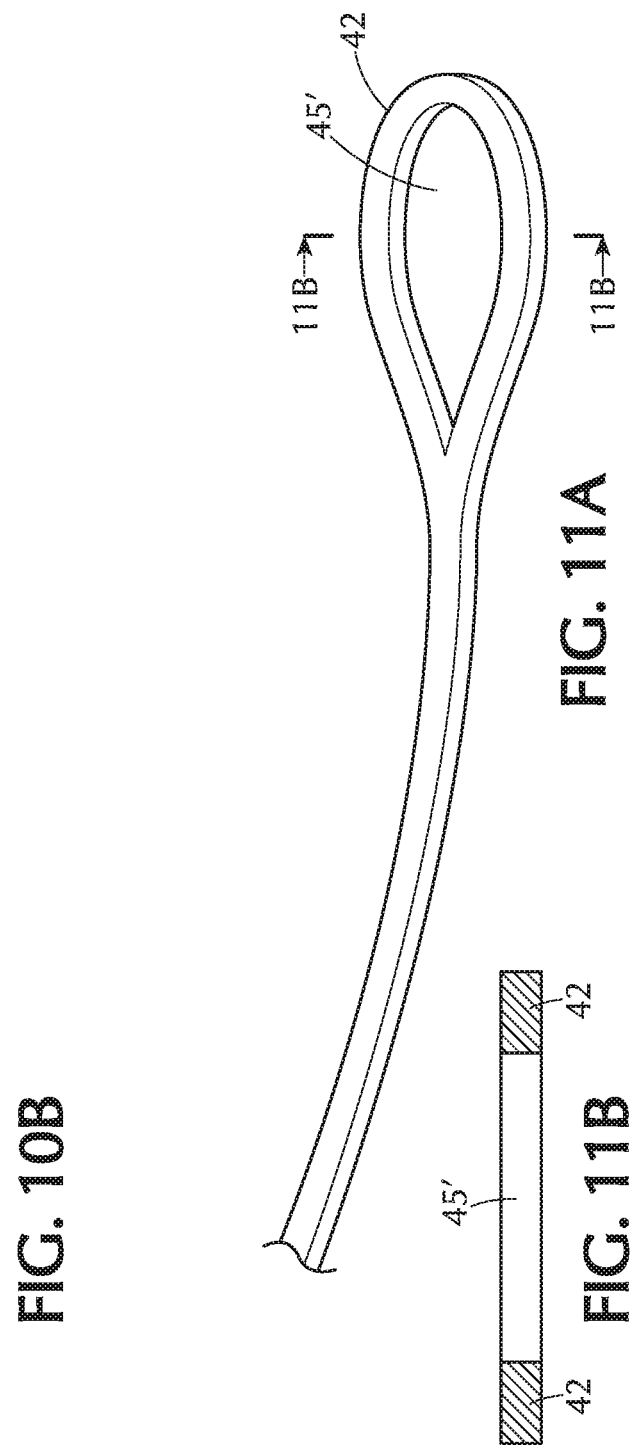

GUIDEWIRE WITH AN ATRAUMATIC CLOT-CIRCUMVENTING CONFIGURED DISTAL END FOR USE IN AN ENDOVASCULAR MEDICAL SYSTEM

CROSS-REFERENCE TO RELATED APPLICATIONS

This application is a divisional application of U.S. patent application Ser. No. 16/003,527, filed Jun. 8, 2018, which is herein incorporated by reference in its entirety.

BACKGROUND OF THE INVENTION

Field of the Invention

The present invention relates to an endovascular medical system advanceable through a vasculature with a distal end configured to minimize trauma to the vasculature tissue and branch vessels. In particular, the present invention is directed to a guidewire used to recanalize an occluded cerebral artery following an acute ischemic stroke, wherein the guidewire incorporates an atraumatic clot-circumventing configured distal end.

Description of Related Art

Acute ischemic stroke is caused by a thrombotic or embolic occlusion (e.g., blockage) in a cerebral artery of the brain. The occlusion is typically caused by a blood clot liberated from another part of the body which travels through the vessel and eventually become lodged in the cerebral artery of the brain. Clots are subject to a pulsatile pressure gradient (i.e., systemic blood pressure acting on the proximal thrombus face minus the pressure from retrograde collateral blood flow at the distal thrombus face) which may compact and further wedge in place the clot within the vessel over time. In addition, some degree of biological adhesion may occur between the clot and the interior wall of the vessel.

A procedure known as a thrombectomy may be used to remove the thrombus, occlusion, blockage or clot lodged in the vessel using a mechanical device. Thrombectomy treatment or procedure is typically performed on patients within a relative short period of time following a stroke (e.g., less than an approximately 48-hour period after the occurrence of a stroke) and is best suited for large vessel occlusions typically with a diameter greater than approximately 1.0 mm. Non-invasive imaging, for example, angiography, mostly CT angiography (CTA), is typically used to determine the clot size to determine if thrombectomy treatment is suitable for that particular patient.

During the thrombectomy procedure or treatment a physician or interventionalist endovascularly introduces a guidewire through the vasculature, typically in an artery located in the groin or by direct access through the carotid artery. The guidewire is advanced through the vasculature to a location facing a proximal side of the targeted clot, blockage or occlusion. Once the guidewire is properly positioned, a microcatheter with an outer diameter typically less than approximately 1.0 mm, tracks over the guidewire passing through a lumen defined axially through the microcatheter.

Guidewires commonly used for these types of procedures are relatively small in diameter so that they may easily pass through a lumen having a relatively small inner diameter defining a lumen extending longitudinally through the microcatheter. Conventional guidewire outer diameter sizes range from approximately 0.010" to approximately 0.014", while the inner diameter range of the lumen of the microcatheter is between approximately 0.016" and approximately 0.027". Typically, the outer diameter of the guidewire used is 0.014", while the inner diameter of the microcatheter is 0.021". Smaller size guidewires having an approximately 0.010" outer diameter and microcatheters having an inner diameter lumen of approximately 0.016" are sometimes used, particularly in smaller or more distal vessels.

Some physicians or interventionalists prefer to advance only the microcatheter across, around or over the clot, while retaining the guidewire distal end or tip within the lumen of the microcatheter on a proximal side facing the clot. That is, the distal end or tip of the guidewire never crosses over or around the clot to its distal side. The rationale being that the relatively soft and relatively flexible distal end of the microcatheter is less traumatic to the vasculature tissue than that of the guidewire. In many cases, due to its flexibility, it is very difficult to advance the microcatheter across, around or over the clot without the aid of the guidewire. To overcome such difficulty, the microcatheter and guidewire may be advanced across the clot together with the distal end or tip of the guidewire positioned inside the distal section of the microcatheter.

Otherwise, the guidewire may be advanced forward across the clot first and then followed by the microcatheter. Referring to FIG. 1, when advanced across the occlusion or clot 3 first, the guidewire 30 may undesirably: (i) enter a perforator vessel 17 that branches from a target, main or primary artery 15 potentially causing vessel damage and perforation; and/or (ii) cause injury or damage to the vessel tissue when passed across the clot. To minimize or prevent injury to the target vessel tissue and/or perforator vessels, when the guidewire is advanced across the clot prior to the microcatheter, the physician or interventionalist may deliberately change or alter the guidewire by bending its distal end or tip 1500 into a curved "J-shape", as depicted in FIGS. 15A-15C, to assist in steering or guiding the microcatheter to its target location or site. The J-shaped distal end or tip 1500 includes a curved section 1505 (forming a curve less than 180°) which terminates in a free terminating end 1510. FIG. 15B depicts the prior art J-shaped distal tip 1500 of the guidewire approaching the clot 3. As the guidewire is pushed forward by the physician the J-shape distal end or tip may deliberately prolapse (i.e., fold in on or over itself) while subject to resistance (e.g. friction) when passing between the inner vessel wall and the clot. In such prolapse configuration, the curved or loop section 1505 passes over the clot or occlusion 3 first thereby prohibiting the free terminating end 1510 from entering the perforator vessel 17 and damaging the vessel tissue. Prolapsing of the J-shaped distal tip only occurs upon being advanced forward against a resistance (e.g., when crossing over the clot between the vessel wall and the clot). That is, the J-shaped distal end or tip is not prolapsed while in a relaxed state (not subject to application of any external mechanical force, friction or resistance). However, shaping or altering of the distal tip or end of the guidewire in such manner is difficult to control by the physician or interventionalist possibly resulting in the shaped or altered distal end or tip being incapable of passing across or around the clot and/or potentially causing deleterious injury or damage to the target vessel tissue when passed (or attempted to be passed) across or around the clot.

The present invention overcomes the aforementioned problems associated with guidewires used in mechanical thrombectomy procedures by configuring an atraumatic clot-circumventing configured distal tip or end of the guidewire to prohibit advancement into one of the perforator vessels, yet easily pass over, across or around an occlusion between the occlusion and the inner wall of the target vessel, without penetrating the occlusion or without injuring the delicate tissue of the target neurovascular vessels.

SUMMARY OF THE INVENTION

An aspect of the present invention is directed to an improved guidewire for use in an endovascular medical procedure (e.g., mechanical thrombectomy) by configuring the distal tip or end of the guidewire to prohibit advancement into a perforator vessel, yet readily pass over, across or around an occlusion between the occlusion and the inner wall of the target vessel without injuring the tissue of the target neurovascular vessels.

Another aspect of the present invention relates an endovascular medical system for use with a clot located in a target vessel. The system including a guidewire formed by a core wire. The guidewire extending in a longitudinal direction from a proximal end to an opposite atraumatic clot-circumventing configured distal end; and a lateral direction of the atraumatic clot-circumventing configured distal end of the guidewire being defined transverse to the longitudinal direction of the guidewire. The atraumatic clot-circumventing configured distal end is designed to prevent injury to an inner wall of the target vessel and prohibit insertion of any portion of the guidewire into a perforator vessel.

Yet another aspect of the present invention is directed to a method for using an endovascular medical system for use with a clot located in a target vessel. The endovascular medical system including a microcatheter having a lumen defined longitudinally therethrough from its proximal end to its opposite distal end, wherein the lumen has an inner diameter. In addition, the endovascular medical system further includes a guidewire formed by a core wire and receivable through the lumen of the microcatheter. The guidewire extends in a longitudinal direction from a proximal end to an opposite atraumatic clot-circumventing configured distal end; a lateral direction of the atraumatic clot-circumventing configured distal end of the guidewire being defined transverse to the longitudinal direction of the guidewire. In accordance with the present invention, the atraumatic clot-circumventing configured distal end is configured to prevent injury to an inner wall of the target vessel and prohibit insertion of any portion of the guidewire into a perforator vessel. The method for using the present inventive system includes advancing the atraumatic clot-circumventing configured distal end of the guidewire through the target vessel to a location facing a proximal side of the clot. Then the microcatheter is tracked over the guidewire received within the lumen of the microcatheter to the location facing the proximal side of the clot. The atraumatic clot-circumventing configured distal end of the guidewire passes between the inner wall of the target vessel and the clot from a position on the proximal side of the clot to a position facing a distal side of the clot, without any portion of the atraumatic clot-circumventing configured distal end of the guidewire penetrating the clot. Thereafter, the microcatheter is guided over the guidewire received within the lumen of the microcatheter to the position facing the distal side of the clot. The microcatheter may also be used to provide support for the introduction of a distal access, guide or intermediate catheter. Now, the guidewire may be removed and a mechanical thrombectomy device such as a stentriever or any other clot retrieval device may be advanced through the microcatheter to the target site of the blockage and used to retrieve the clot or occlusion to the guide catheter or sheath.

BRIEF DESCRIPTION OF THE DRAWING

The foregoing and other features of the present invention will be more readily apparent from the following detailed description and drawings of illustrative of the invention wherein like reference numbers refer to similar elements throughout the several views and in which:

FIG. 5A is still another exemplary illustration of the atraumatic clot-circumventing configured distal tip or end of a guidewire in accordance with the invention, wherein the atraumatic clot-circumventing configured distal tip or end of the guidewire is a flattened portion of the core wire cut or stamped into a paddle shape; the paddle shaped distal tip or end is illustrated in FIG. 5A in a relaxed or non-compressed state (not subject to application of an external mechanical force);

FIG. 5B is a cross-sectional view of the paddle shaped atraumatic clot-circumventing configured distal tip or end of the guidewire in FIG. 5A along lines 5B-5B;

FIG. 6 depicts the paddle shaped atraumatic clot-circumventing configured distal end or tip of the guidewire of FIG. 5A while in a relaxed or non-compressed state (not subject to application of an external mechanical force) and a microcatheter guided over the guidewire which is received in the lumen of the microcatheter;

FIG. 7 depicts the paddle shaped atraumatic clot-circumventing configured distal end or tip of the guidewire of FIG. 5A in a compressed state (i.e., subject to an applied external mechanical force exerted by the inner wall of the lumen of the microcatheter) when the guidewire is retracted or drawn back through the microcatheter; opposing lateral edges of the paddle shaped atraumatic clot-circumventing configured distal end or tip are wrapped, curled or rolled towards one another thereby reducing its diameter to be receivable within the inner diameter of the lumen of the microcatheter;

FIG. 10A is one exemplary configuration of the flattened paddle shaped atraumatic clot-circumventing configured distal tip or end of the core wire of the guidewire while in a relaxed or non-compressed state (not subject to application of an external mechanical force);

FIG. 10B is a cross-sectional view of the flattened paddle shaped atraumatic clot-circumventing configured distal tip or end of the guidewire in FIG. 10A along lines 10B-10B;

FIG. 11A is another exemplary configuration of the flattened paddle shaped atraumatic clot-circumventing configured distal tip or end of the core wire of the guidewire with a single central portion removed defining an eyelet or opening having a closed perimeter; wherein the flattened paddle shaped atraumatic clot-circumventing configured distal tip or end of the core wire of the guidewire is in a relaxed or non-compressed state (not subject to application of an external mechanical force);

FIG. 11B is a cross-sectional view of the flattened paddle shaped atraumatic clot-circumventing configured distal tip or end of the guidewire in FIG. 11A along lines 11B-11B;

DETAILED DESCRIPTION OF THE INVENTION

The terms "distal" or "proximal" are used in the following description with respect to a position or direction relative to the treating physician or medical interventionalist. "Distal" or "distally" are a position distant from or in a direction away from the physician or interventionalist. "Proximal" or "proximally" or "proximate" are a position near or in a direction toward the physician or medical interventionist. The terms "occlusion", "clot" or "blockage" are used interchangeably.

Figure 4:
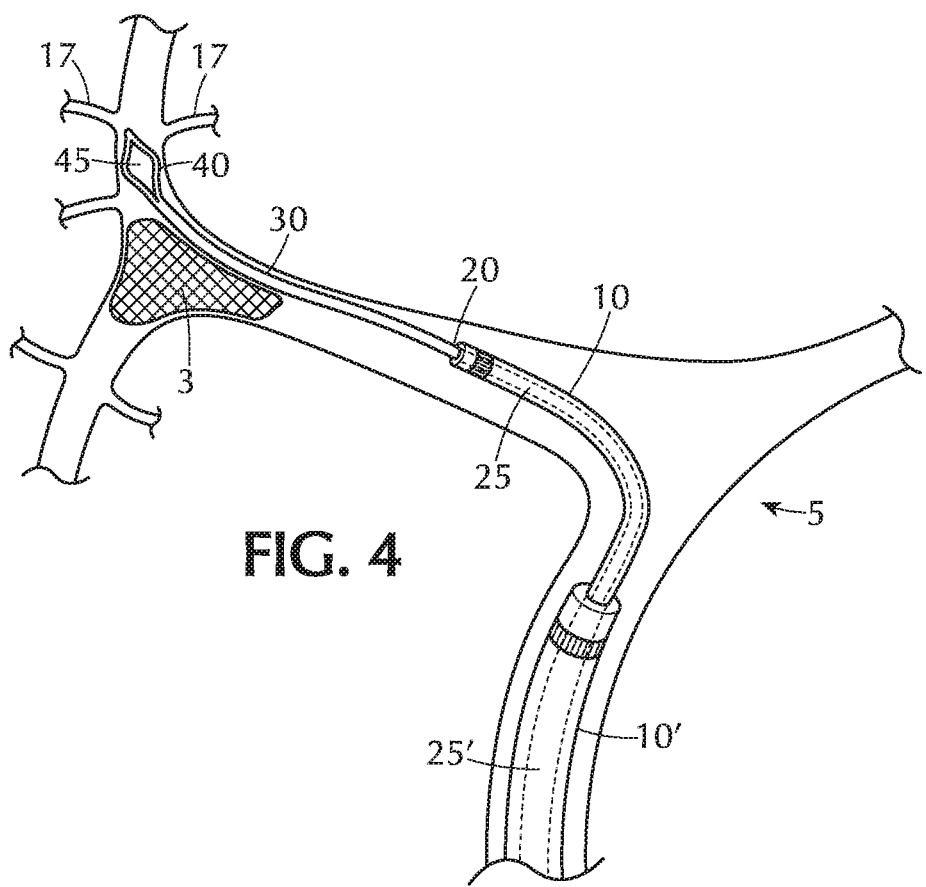
FIG. 4 is an exemplary illustration of the present inventive mechanical thrombectomy system wherein the atraumatic clot-circumventing configured distal tip of the guidewire of FIG. 2A is advanced through a target vessel over a blockage between the target vessel wall and the blockage, wherein the atraumatic clot-circumventing configured distal tip or end of the guidewire is prohibited from entering a perforator vessel after passing over or around the clot.

As illustrated in FIG. 4, the present inventive mechanical thrombectomy system 5 includes a microcatheter 10 having a lumen 25 defined in a longitudinal direction therethrough from its distal end 20 to its opposite proximal end. Microcatheter 10 may itself be received or advanced through a lumen 25' defined longitudinally through a distal access, intermediate or guide catheter 10'. A guidewire 30 formed by a core wire has a distal end or tip 40 and an opposite proximal end defining a longitudinal direction therebetween. A lateral direction being defined transverse to the longitudinal direction of the guidewire. In accordance with the present invention, distal end or tip 40 of the guidewire 30 has an atraumatic clot-circumventing configuration. In accordance with the present invention, the term "atraumatic clot-circumventing configuration" can be any geometric shape and preferably satisfies the following three conditions. The first condition being that the atraumatic clot-circumventing configured distal end of the guidewire, while in a relaxed or non-compressed state, has a widest transverse width in a lateral direction (i.e., transverse to the longitudinal direction extending from the proximal end to the distal end of the guidewire) greater than the inner diameter of the lumen of the microcatheter through which the guidewire is received. Preferably, the widest transverse width is approximately twice the inner diameter of the microcatheter. Therefore, the preferred range of the widest transverse width is approximately 0.030"-approximately 0.050" for a microcatheter having an inner diameter of 0.021". This enlarged widest traverse width of the distal end or tip of the guidewire prohibits its insertion into a perforator vessel and thus, prevents injury or damage to the vessel tissue therein. A second condition being that the atraumatic clot-circumventing configured distal end of the guidewire is conformable in a lateral direction to complement the contour of the inner wall of the target vessel. Thus, when guidewire is advanced through the target vessel across, around or over the blockage passing between the inner wall of the target vessel and the blockage, no portion of the blockage is penetrated by the guidewire and the guidewire is atraumatic (not causing injury or damage) to the target vessel wall. The third condition to be satisfied by the atraumatic clot-circumventing configured distal end of the guidewire being that its widest traverse width in the lateral direction, when subject to application of an external mechanical force, is reducible in diameter to fit within the lumen of the microcatheter.

The atraumatic clot-circumventing configured distal end or tip 40 of the guidewire 30 may be pre-shaped by the physician or interventionalist or pre-formed. A non-super elastic material (i.e., a shaped memory alloy material that fails to meet the definition of a super elastic shape memory material provided below) may be used allowing the physician or interventionalist to pre-shape the distal end or tip of the core wire proximal to its atraumatic distal tip. Otherwise, a core wire made of a super elastic shaped memory material (i.e., a shaped memory alloy material that is reversibly deformable to very high strains (up to approximately 10%)) such as nitinol (NiTi) may be pre-formed, for example, by heat-setting during the manufacturing process. The entire guidewire may comprise this super elastic material as its core wire making it more durable, and thus suitable for re-use if multiple passes across the occlusion, clot or blockage are required.

Numerous variations or configurations of the present inventive atraumatic clot-circumventing configured distal end or tip 40 of the guidewire 30 are contemplated. Several illustrative examples are shown in the drawings and described in detail below. Other configurations are possible and thus the present invention is not to be limited only to those examples shown and described.

Figure 2A:
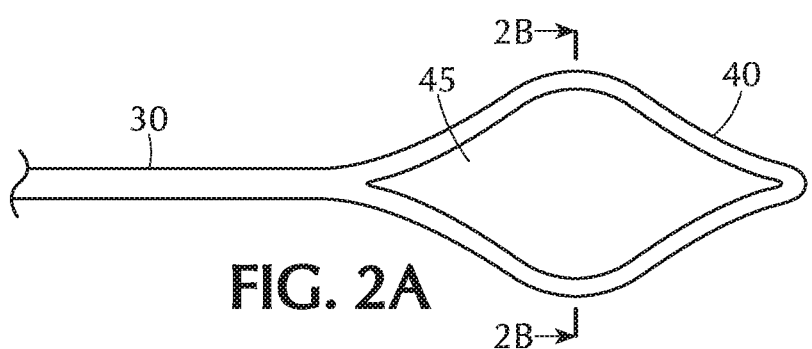
FIG. 2A is an exemplary illustration of a guidewire having an atraumatic clot-circumventing configured distal tip or end in accordance with the present invention, wherein the atraumatic clot-circumventing configured distal tip or end is the core wire bent into a lemon-shape configuration with a central opening or eyelet; wherein the guidewire in FIG. 2A is illustrated in a relaxed or non-compressed state (not subject to application of an external mechanical force)
Figure 2B:
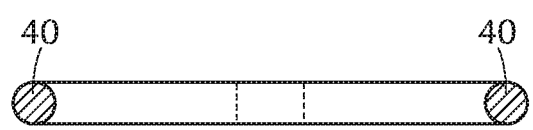
FIG. 2B is a cross-sectional view of the atraumatic clot-circumventing configured distal tip or end of the guidewire in FIG. 2A along lines 2B-2B.

FIG. 2A in an enlarged partial view of an exemplary pre-formed atraumatic clot-circumventing configured distal end or tip 40 of the guidewire 30 in FIG. 4, while in a relaxed or non-compressed state (i.e., not subject to application of an external mechanical force). In this exemplary embodiment, the atraumatic clot-circumventing configured distal end or tip 40 of the core wire of the guidewire is pre-formed into a configuration resembling a lemon-shape forming a closed loop. A single eyelet or opening 45 is defined in the atraumatic clot-circumventing configured distal end or tip 40. Depicted in FIG. 2B, is a cross-sectional view along lines 2B-2B of FIG. 2A through the widest traverse width in a lateral direction of the pre-formed core wire.

Figure 1:
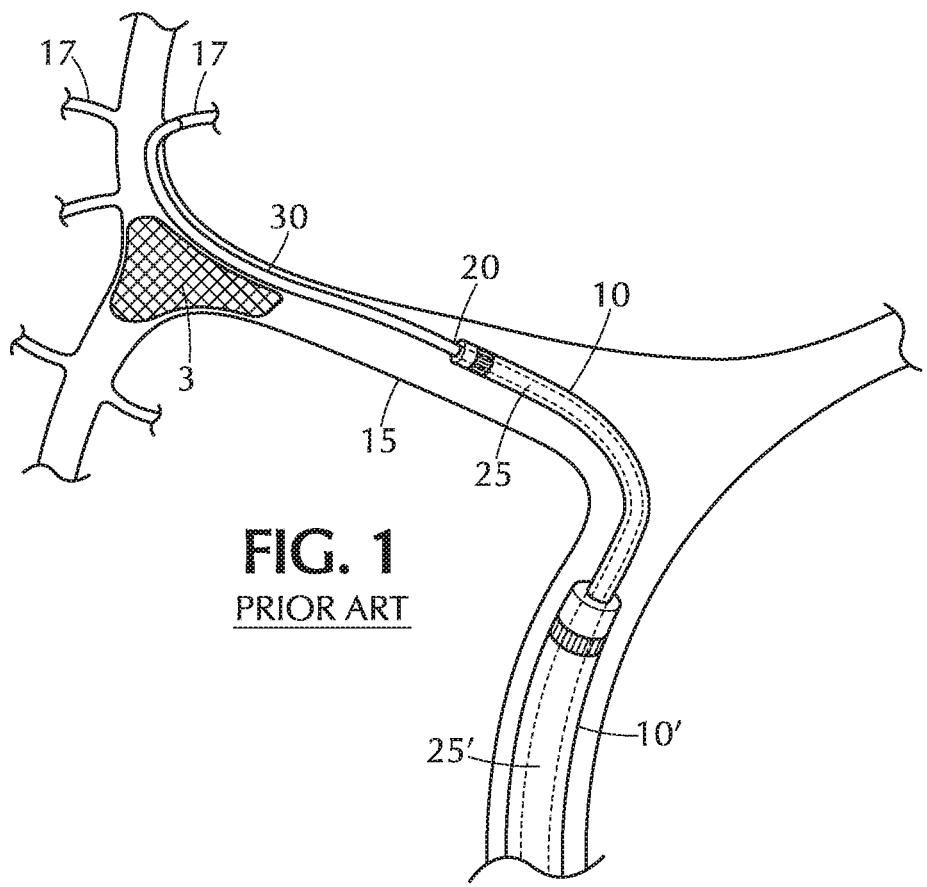
FIG. 1 is an exemplary prior art conventional mechanical thrombectomy system including a guidewire having a conventional distal tip or end undesirably introduced into a perforator vessel after crossing through a clot, occlusion or blockage.
Figure 3A:
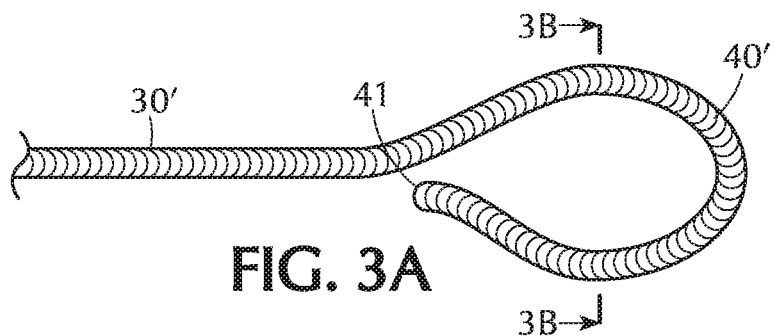
FIG. 3A is another exemplary illustration of an atraumatic clot-circumventing configured distal tip or end of the guidewire in accordance with the present invention, wherein the atraumatic clot-circumventing configured distal end or tip is the core wire bent into a shepherd's crook shape configuration; wherein the guidewire in FIG. 3A is illustrated in a relaxed or non-compressed state (not subject to application of an external mechanical force)
Figure 3B:
FIG. 3B is a cross-sectional view of the atraumatic clot-circumventing configured distal tip or end of the guidewire in FIG. 3A along lines 3B-3B.

An enlarged partial view of another exemplary atraumatic clot-circumventing configured distal end or tip 40' in which the core wire 30' is pre-shaped into an open loop configured as a hook or shepherd's crook is depicted in FIGS. 3A & 3B. When forming the pre-shaped hook or shepherd's crook atraumatic clot-circumventing configured distal end or tip 40' of the guidewire, the free terminating end 41 extends in a direction back towards the proximal end of the guidewire to form a curved open loop section that is greater than 180° (while in a relaxed, non-compressed state not subject to application of an external mechanical force). This configuration prohibits any portion of the atraumatic clot-circumventing configured distal end of the guidewire from entering the perforator vessel. In addition, the present inventive tip of the core wire bent backwards (i.e., prolapsed) towards the proximal end forming a curved open loop section greater than 180 degrees provides a curved surface rather than a single point (as with the blunt tip end of the conventional guidewire illustrated in FIG. 1). The surface of the pre-shaped distal end is atraumatic preventing injury to the target vessel tissue while ensuring that the guidewire passes between the occlusion and inner wall of the target vessel, rather than penetrating the occlusion itself.

In the embodiment illustrated in FIG. 3A, the physician or interventionalist grasps the free terminating end 41 and straightens the pre-shaped hook or shepherd's crook distal end or tip prior to insertion of the free terminating end 41 into the lumen 25 at the proximal end of the microcatheter 10. The distal end or tip of the guidewire maintains its straightened configuration or state while being advanced through the lumen of the microcatheter. Upon exiting from the distal end of the microcatheter, the distal end 40' of the guidewire automatically reverts to its original curved pre-shaped hook or shepherd's crook configuration, as depicted in FIG. 3A (relaxed or non-compressed state not subject to application of an external mechanical force).

Rather than pre-forming or pre-shaping the core wire to form a desired geometric shape as depicted in FIGS. 2A & 3A, a distal portion of the core wire (having a circular lateral cross-section) may alternatively be flattened out and then cut or stamped into a desired geometric shape to form the atraumatic clot-circumventing configured distal end or tip. In the exemplary embodiment shown in FIG. 5A, hereinafter referred to as a "planar paddle shape" 40", the core wire is flattened so that it is substantially planar and its thickness reduced relative to the circular diameter of that remaining portion (non-flattened out portion) of the core wire. Once flattened out to a desired thickness, the planar distal end or tip is then cut or stamped into a desired shape (e.g., paddle shape) to form a thin support structure or substrate 50, typically having a thickness ranging from approximately 0.0005" to approximately 0.010", preferably the thickness ranges from approximately 0.001" to approximately 0.005". The paddle shape distal end or tip may alternatively be achieved by assembling a pre-formed planar paddle shaped distal end or tip, having the same specified thickness range, on an end of a separate core wire, such as by welding, soldering or bonding. Two separate components assembled or joined together is particularly well suited to applications in which the pre-formed planar paddle and core wire on which the paddle is to be assembled are made of different materials. As illustrated in the cross-sectional view in FIG. 5B, an outer covering or layer 55 may be applied to the external surface of the supporting structure 50. Outer covering or layer 55 may comprise one or more coverings, coating layers, or films. For instance, the outer covering or layer 55 may comprise a polymer jacket applied directly to the outer surface of the support structure or substrate 50 with or without a lubricious coating, e.g., a hydrophilic material, applied directly to the outer surface of the polymer jacket. The outer jacket may also contain radiopaque fillers to enhance fluoroscopic visibility of the tip.

The planar paddle shaped distal end or tip 40" may have an asymmetrical design along its longitudinal axis 60 (FIG. 6) extending in a direction from a proximal end to a distal end of the guidewire. Such asymmetrical design aids wrapping, curling, or rolling of the opposing lateral edges of the paddle shaped distal end or tip towards one another into a tube or cylinder as the guidewire is retracted backwards through the lumen 25 of the microcatheter 10. As a result, the guidewire may be retracted or drawn back through the distal end of the microcatheter with minimal force. This wrapping, curling or rolling of the lateral edges of the planar paddle shaped distal end or tip 40" within the lumen of the microcatheter is akin to that of rolling one's tongue. FIG. 7 is a partial view illustration of the planar paddle shaped distal end or tip 40" retracted or drawn back into the lumen of the microcatheter through its distal end 20 causing the lateral edges of the paddle to wrap, curl or roll towards one another. When wrapped, curled or rolled towards one another, the opposing lateral edges may, but need not necessarily, physically contact one another. Moreover, it is contemplated and within the intended scope of the present invention for the lateral edges to overlap one another when wrapped curled or rolled which beneficially allows a wider width paddle to fit within the lumen of the microcatheter. Upon exiting from the lumen 25 of the microcatheter 10, the paddle shaped distal end or tip 40" of the guidewire is automatically restored to its former planar relaxed or non-compressed state (not subject to application of an external mechanical force) (as depicted in FIG. 5A).

The paddle is sized such that, while in its relaxed or uncompressed state (not subject to an applied external mechanical force) as depicted in FIGS. 5A & 6, its widest transverse width (WW) along a lateral direction 65 (transverse to that of the longitudinal direction 60 from the proximal end to the distal end of the guidewire) is greater than an inner diameter (ID) of the lumen 25 of the microcatheter 10 and wider than the diameter of the perforator vessels that the paddle is intended to prevent the guidewire from entering. The maximum widest transverse width is approximately twice the inner diameter of the microcatheter. For example, a paddle having a widest transverse width (WW) while in a relaxed or non-compressed state is preferably in the range of approximately 0.030" to approximately 0.050" for a microcatheter having an inner diameter of approximately 0.021".

The paddle shaped distal end is also sufficiently flexible, based on the material used and its flattened thickness, so that when the guidewire is retracted or drawn back through the microcatheter the smaller inner diameter (ID) of the lumen applies an external mechanical force on the paddle shaped distal end causing it to curl and reduce in diameter smaller than the inner diameter of the lumen. Despite being larger in size, the paddle while in this compressed state can pass easily through the lumen 25 of the microcatheter 10, as represented in FIG. 7. In this compressed state, the widest diameter (WD) of the wrapped, curled or rolled paddle shaped distal end is slightly smaller than the inner diameter (ID) of the lumen 25 of the microcatheter 10.

Figure 12A:
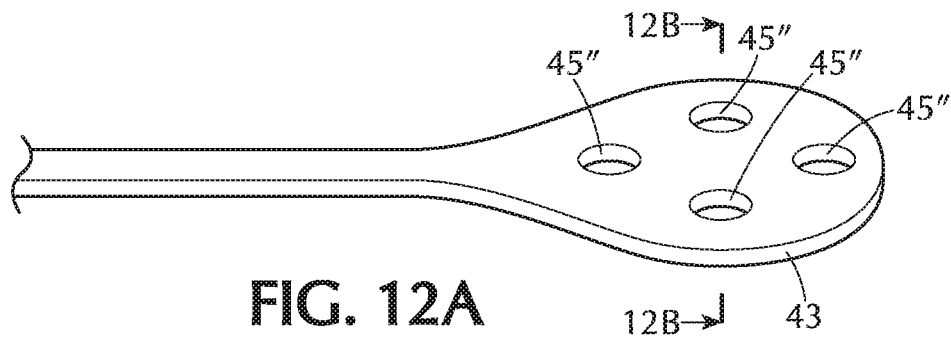
FIG. 12A is still another exemplary configuration of the flattened paddle shaped atraumatic clot-circumventing configured distal tip or end of the core wire of the guidewire with multiple portions removed defining plural openings each of which has a closed perimeter; wherein the flattened paddle shaped atraumatic clot-circumventing configured distal tip or end of the core wire of the guidewire is in a relaxed or non-compressed state (not subject to application of an external mechanical force)
Figure 12B:
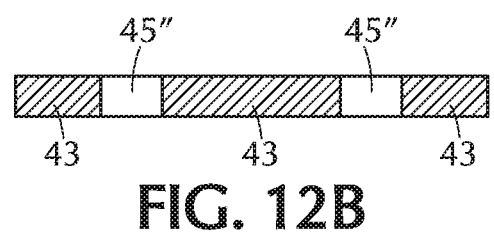
FIG. 12B is a cross-sectional view of the flattened paddle shaped atraumatic clot-circumventing configured distal tip or end of the guidewire in FIG. 12A along lines 12B-12B.

The flattened distal end of the core wire, after having been cut, stamped or assembled into its paddle shape (FIGS. 10A & 10B), may be further modified by removing (e.g., cutting or stamping) material within the flattened paddle shaped form. Removal of such material from the flattened paddle shaped distal end or tip advantageously: (i) increases flexibility so that the distal end or tip of the guidewire is able to more easily navigate between the clot and inner wall of the target vessel while also minimizing the force necessary to retract or draw back the paddle shaped distal end or tip through the lumen of the microcatheter; and (ii) is better suited to integrate a polymer jacket or other outer covering, layer or film over the flattened paddle shaped distal end or tip. A single central portion may be removed from the flattened paddle shaped distal end tip. In the example illustrated in FIGS. 11A & 11B, a single eyelet or opening 45' conforming in shape to that of the outer perimeter of the paddle. It is noted that the opening 45' need not be centrally located nor conform to the shape of the paddle. Another example is shown in FIGS. 12A & 12B, wherein material is removed from within the paddle form in more than one region defining four openings 45". The paddle may be designed, as desired, to have any number of one or more openings, each of which may, but is not required, to conform in shape with the other openings and/or with that of the outer contour of the paddle.

Figure 8A:
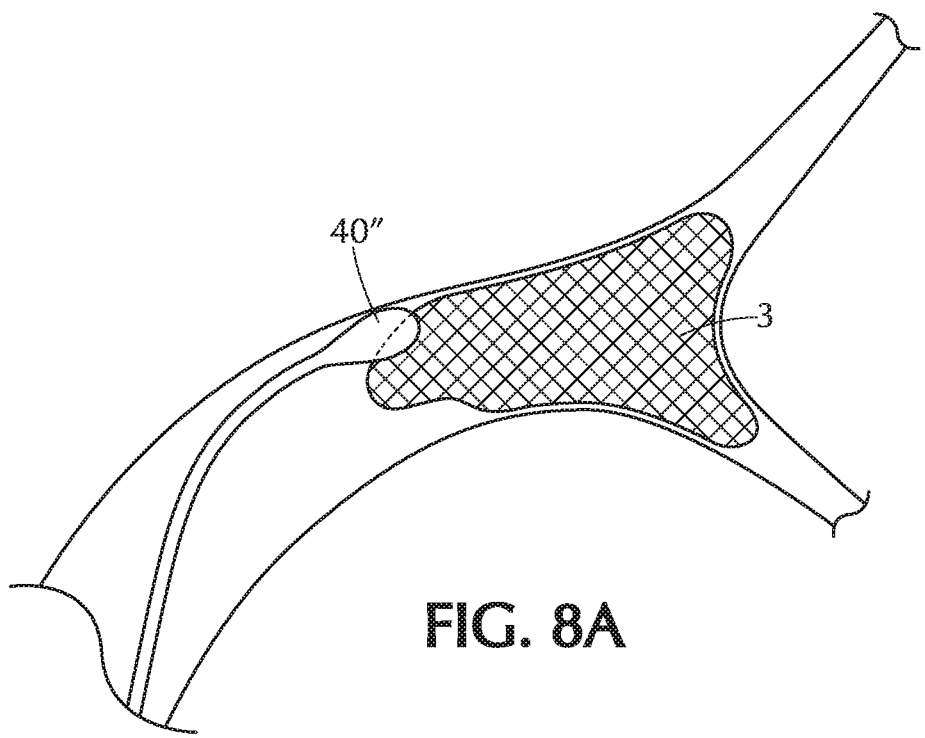
FIGS. 8A-8C illustrate the paddle shaped atraumatic clot-circumventing configured distal end or tip of the guidewire of FIG. 5A as it advances over, around or across a clot between the inner wall of the target vessel and the clot, wherein the paddle shaped atraumatic clot-circumventing configured distal end or tip of the guidewire conforms in shape complementary to that of the inner wall of the target vessel.
Figure 8B:
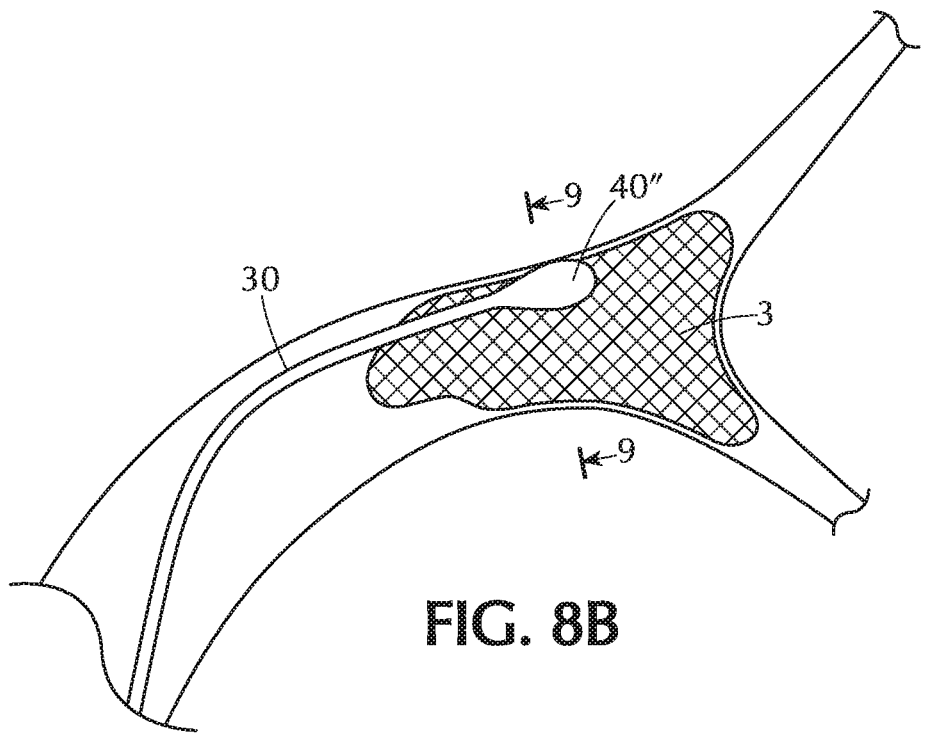
Figure 8C:
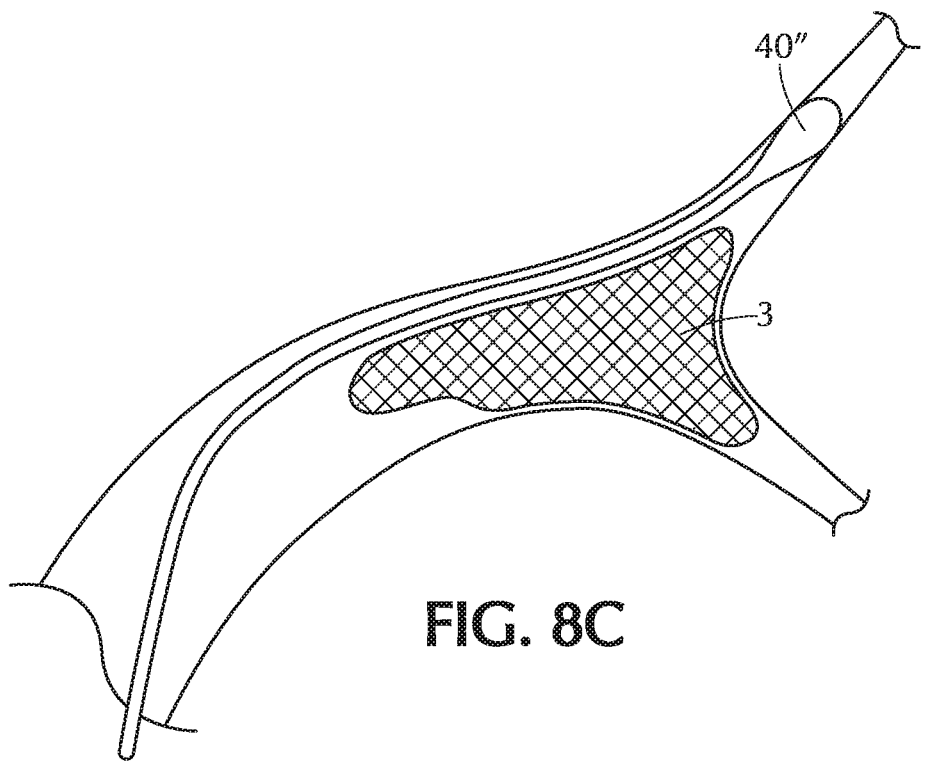
Figure 9:
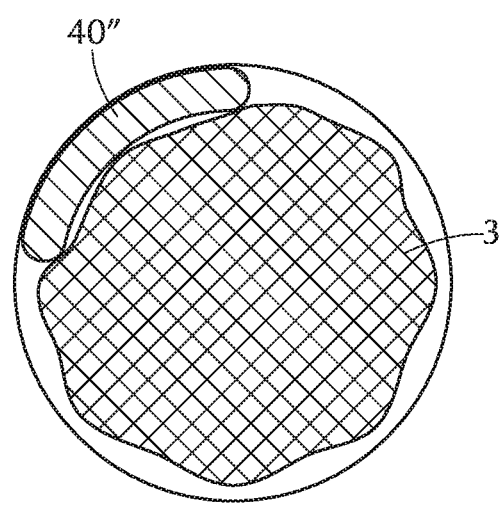
FIG. 9 is a cross-sectional view of the vessel along lines 9-9 of FIG. 8B illustrating how the paddle shaped atraumatic clot-circumventing configured distal end or tip of the guidewire of FIG. 5A conforms to the shape of the inner wall of the vessel.

FIGS. 8A-8C are partial illustrations of the flattened paddle shaped distal end guidewire of FIG. 5A as it passes across the clot or occlusion 3 lodged in the vessel. As is depicted in the cross-sectional view of FIG. 9, the flattened paddle shaped distal end 40" of the guidewire passes over or around the clot 3 at the interface between the clot and the inner wall of the target vessel without penetrating any portion of the clot. Since the paddle shaped distal end forms a surface rather than a point, the guidewire can easily navigate between the inner wall of the target vessel and the clot without injury to the tissue of the target vessel. Moreover, the enlarged width of the paddle while in a relaxed or non-compressed state (not subject to application of an external mechanical force) ensures that the guidewire after passing across, over or around the clot will not enter a perforator vessel. The paddle shaped distal end of the guidewire, as shown in FIG. 9, easily adapts to conform in shape to the inner wall of the vessel. This ability may reduce the force required to cross over or around the clot and more easily cross over or around more challenging fibrin rich or dense clots.

Figure 13:
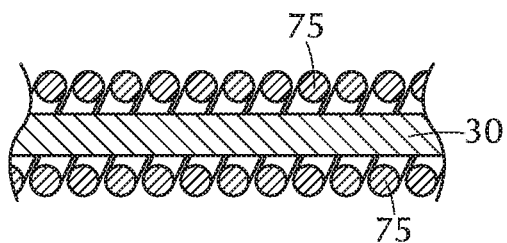
FIG. 13 is a partial cross-sectional view of the guidewire core having one or more coils disposed about its outer surface.
Figure 14:
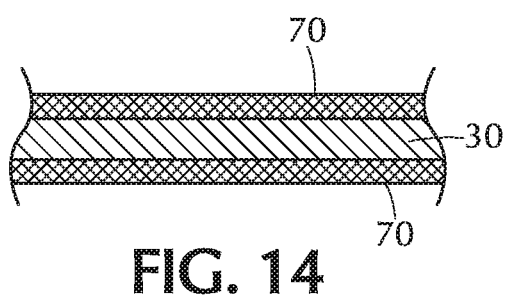
FIG. 14 is a partial cross-sectional view of the guidewire core covered by a polymer jacket, coating or outer layer.
Figure 15A:
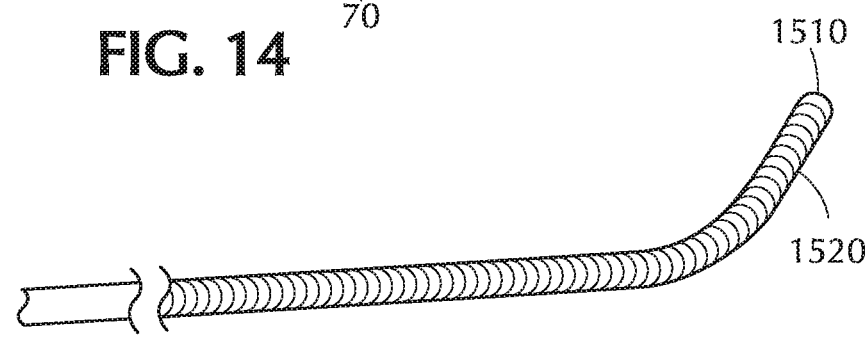
FIG. 15A is a partial perspective view of a Prior Art J-shaped tip of a guidewire.
Figure 15B:
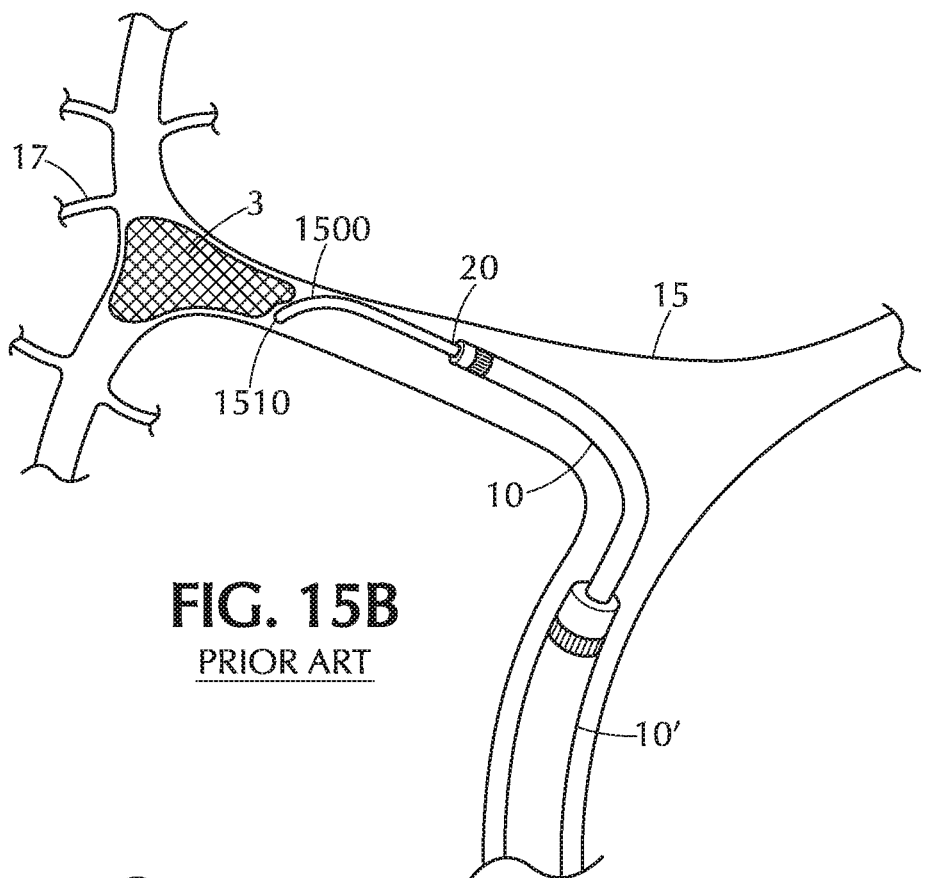
FIG. 15B depicts the Prior Art J-shaped tip guidewire of FIG. 15A as it approaches a clot (on the proximal side of the clot)
Figure 15C:
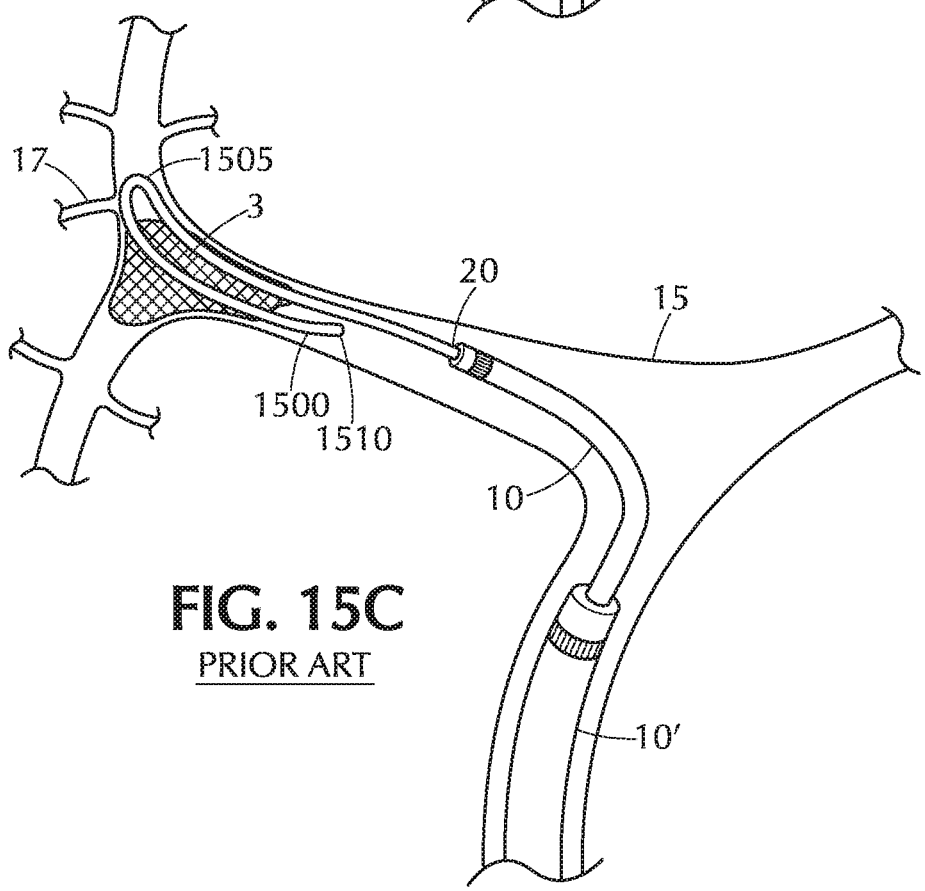
FIG. 15C depicts the Prior Art J-shaped tip guidewire of FIG. 15A prolapsing as it crosses over the clot so that the curved loop section crosses the clot first, rather than the free terminating end.

To aid visibility the core wire of the guidewire may be covered with a radiopaque material visible under imaging (e.g., under fluoroscopy). For example, a polymer jacket or outer covering 70 containing a radiopaque additive or filler may be applied directly to the outer surface of the guidewire 30 (FIG. 14) and/or outer coils 75 (e.g., made of platinum alloy or other radiopaque material) wound about the outer surface of the guidewire 30, as illustrated in FIG. 13.

In operation, such as during a thrombectomy procedure or treatment, a physician or interventionalist endovascularly introduces into a target vessel, typically in an artery located in the groin, a guidewire having an atraumatic clot-circumventing configured distal end or tip in accordance with the present invention. The guidewire is advanced through the vasculature to a location facing a proximal side of the targeted clot, blockage or occlusion. Once the guidewire is properly positioned, a microcatheter tracks over the guidewire passing through a lumen defined axially through the microcatheter. The present inventive atraumatic clot-circumventing configured distal tip of the guidewire is advanced across the clot first and then followed by the microcatheter. Because of the present inventive atraumatic clot-circumventing configured and sized distal end or tip, the guidewire easily passes around or over the clot without injury to the neurovasculature tissue of the target vessel, yet prevents the guidewire from entering a perforator vessel upon reaching the distal side of the clot. Once the distal end of the guidewire is properly positioned on the distal side of the clot, the microcatheter tracks over the guidewire crossing around or over the clot to its distal side. With the microcatheter positioned on the distal side of the clot, the guidewire may be retracted or withdrawn proximally backwards through the microcatheter, while the microcatheter remains in place. The microcatheter can also be used to provide support for the introduction of a distal access, guide or intermediate catheter. A mechanical thrombectomy device such as a stentriever or any other clot retrieval device can be advanced through the microcatheter to the target site of the blockage and used to retrieve the clot or occlusion to the guide catheter or sheath.

The present inventive guidewire has been illustrated and described for use in a mechanical thrombectomy procedure but is applicable for use in all neurovascular or endovascular medical procedures that employ guidewires.

Thus, while there have been shown, described, and pointed out fundamental novel features of the invention as applied to a preferred embodiment thereof, it will be understood that various omissions, substitutions, and changes in the form and details of the systems/devices illustrated, and in their operation, may be made by those skilled in the art without departing from the spirit and scope of the invention. For example, it is expressly intended that all combinations of those elements and/or steps that perform substantially the same function, in substantially the same way, to achieve the same results be within the scope of the invention. Substitutions of elements from one described embodiment to another are also fully intended and contemplated. It is also to be understood that the drawings are not necessarily drawn to scale, but that they are merely conceptual in nature. It is the intention, therefore, to be limited only as indicated by the scope of the claims appended hereto.

Every issued patent, pending patent application, publication, journal article, book or any other reference cited herein is each incorporated by reference in their entirety.

What is claimed is:

1. An endovascular medical system for use with a clot located in a target vessel, the system comprising:
   a guidewire formed by a core wire, the guidewire extending in a longitudinal direction from a proximal end to an opposite atraumatic clot-circumventing configured distal end; and a lateral direction of the atraumatic clot-circumventing configured distal end of the guidewire being defined transverse to the longitudinal direction of the guidewire; wherein the atraumatic clot-circumventing configured distal end is designed to prevent injury to an inner wall of the target vessel and prohibit insertion of any portion of the guidewire into a perforator vessel.

2. The endovascular medical system according to claim 1, wherein the atraumatic clot-circumventing configured distal end of the guidewire satisfies the following conditions:
   (i) the atraumatic clot-circumventing configured distal end of the guidewire is conformable in the lateral direction complementary to a contour of the inner wall of the target vessel when passed between the inner wall of the target vessel and the clot; and
   (ii) when in a compressed state subject to application of an external mechanical force, a widest width in the lateral direction of the atraumatic clot-circumventing configured distal end of the guidewire is reducible.

3. The endovascular medical system according to claim 2, further comprising:
   a microcatheter having a lumen defined longitudinally therethrough from its proximal end to its opposite distal end, the lumen having an inner diameter;
   wherein the guidewire is receivable through the lumen of the microcatheter; and
   while in a non-compressed state not subject to application of an external mechanical force, the atraumatic clot-circumventing distal end of the guidewire having the widest width in the lateral direction greater than twice the inner diameter of the lumen.

4. The endovascular medical system according to claim 1, wherein the atraumatic clot-circumventing configured distal end of the guidewire is a flattened distal portion of the core wire having a planar geometric shape and thickness less than an outer diameter of a remaining non-flattened portion of the core wire.

5. The endovascular medical system according to claim 4, wherein the flattened distal portion of the core wire has a paddle geometric shape.

6. The endovascular medical system according to claim 4, wherein the flattened distal portion has at least one aperture defined therein.

7. The endovascular medical system according to claim 1, wherein the atraumatic clot-circumventing configured distal end of the guidewire is the core wire pre-formed or pre-shaped into a geometric shape.

8. The endovascular medical system according to claim 7, wherein the geometric shape of the pre-formed or pre-shaped core wire is a closed loop.

9. The endovascular medical system according to claim 8, wherein the closed loop forms a lemon-shape.

10. The endovascular medical system according to claim 7, wherein the geometric shape of the atraumatic clot-circumventing configured distal end while in a non-compressed state not subject to application of an external mechanical force is an open loop forming a curved section greater than 180° having a free terminating end; and while in the non-compressed state not subject to the external mechanical force, the atraumatic clot-circumventing configured distal end is in a prolapsed configuration.

11. The endovascular medical system according to claim 10, wherein the open loop forming the curved section greater than 180° provides a curved surface.

12. The endovascular medical system according to claim 1, wherein the guidewire and the atraumatic clot-circumventing configured distal end are separate components assembled together.

13. The endovascular medical system according to claim 1, wherein the atraumatic clot-circumventing configured distal end of the guidewire is transitionable between a non-compressed state and a compressed state; and wherein in the non-compressed state the atraumatic clot-circumventing configured distal end of the guidewire has a non-curved radial cross-section.

14. The endovascular medical system according to claim 1, wherein the atraumatic clot-circumventing configured distal end of the guidewire is transitionable between a non-compressed state and a compressed state; and wherein in the compressed state opposing sides in the lateral direction of the atraumatic clot-circumventing configured distal end are curled towards one another to form a curved radial cross-section.

15. The endovascular medical system according to claim 14, wherein in the compressed state the opposing sides in the lateral direction of the atraumatic clot-circumventing configured distal end are curled towards one another so as to physically contact or overlap each other.

16. The endovascular medical system according to claim 14, wherein in the compressed state the opposing sides in the lateral direction of the atraumatic clot-circumventing configured distal end are curled towards each other without physically contacting or overlapping each other.

* * * * *